(12) United States Patent
Dupoteau et al.

(10) Patent No.: US 8,852,505 B2
(45) Date of Patent: Oct. 7, 2014

(54) HEMATOLOGICAL ANALYZER ON WHOLE BLOOD WITH STIRRING DEVICE

(75) Inventors: Francois Dupoteau, Montpellier (FR); Roger Le Comte, Perols (FR); Guilhem Couderc, Saint Jean de Vedas (FR)

(73) Assignee: Horiba ABX SAS, Montpellier (FR)

( * ) Notice: Subject to any disclaimer, the term of this patent is extended or adjusted under 35 U.S.C. 154(b) by 669 days.

(21) Appl. No.: 10/569,647

(22) PCT Filed: Aug. 6, 2004

(86) PCT No.: PCT/FR2004/002105
§ 371 (c)(1),
(2), (4) Date: Oct. 24, 2006

(87) PCT Pub. No.: WO2005/022168
PCT Pub. Date: Mar. 10, 2005

(65) Prior Publication Data
US 2007/0048185 A1    Mar. 1, 2007

(30) Foreign Application Priority Data

Aug. 26, 2003 (FR) ..................................... 03 10175

(51) Int. Cl.
| | |
|---|---|
| *G01N 35/10* | (2006.01) |
| *B01F 9/00* | (2006.01) |
| *B01F 11/00* | (2006.01) |
| *G01N 33/49* | (2006.01) |
| *G01N 35/00* | (2006.01) |

(52) U.S. Cl.
CPC ............ *G01N 35/1079* (2013.01); *B01F 9/002* (2013.01); *B01F 11/0037* (2013.01); *B01F 11/0017* (2013.01); *B01F 11/0002* (2013.01); *B01F 11/0022* (2013.01); *G01N 33/49* (2013.01); *G01N 2035/00524* (2013.01)
USPC ............... 422/63; 422/68.1; 436/43; 366/140

(58) Field of Classification Search
CPC ................ G01N 35/1079; B01N 2035/00524; B01F 9/002; B01F 11/0037; B01F 11/0017; B01L 9/06
See application file for complete search history.

(56) References Cited

U.S. PATENT DOCUMENTS 3,614,434 A * 10/1971 Horwitz et al. ............... 250/364
4,475,411 A * 10/1984 Wellerfors ................. 73/864.24

(Continued)

FOREIGN PATENT DOCUMENTS

| EP | 1 174 717 | 1/2002 |
|---|---|---|
| JP | 2002-98704 | * 4/2002 |

OTHER PUBLICATIONS

U.S. Appl. No. 10/564,784, filed Jan. 17, 2006, Le Comte.

*Primary Examiner* — P. Kathryn Wright
(74) *Attorney, Agent, or Firm* — Oblon, Spivak, McClelland, Maier & Neustadt, L.L.P.

(57) ABSTRACT

A hematological analyzer on whole blood, for analyzing bloods contained in tubes, wherein the tubes are brought and treated in tube mode by the tube. The analyzer includes a stirring device for receiving a blood tube and stirring the blood tube according to a selected stirring mode, a controller connected to the stirring device for stirring the blood tube under conditions controlled according to specific parameters, and a sampling mechanism for extracting a blood sample in the blood tube previously stirred by the stirring device and transferring the blood sample to an analyzing unit. The analyzer is applicable in particular to hematological analyzers for blood cell count.

8 Claims, 4 Drawing Sheets

(56) References Cited

U.S. PATENT DOCUMENTS

| | | | |
|---|---|---|---|
| 4,518,264 A | 5/1985 | Nohso | |
| 4,609,017 A * | 9/1986 | Coulter et al. | 141/1 |
| 4,921,676 A | 5/1990 | Otani | |
| 5,036,989 A * | 8/1991 | Carilli | 211/74 |
| 5,080,864 A * | 1/1992 | Shaw | 422/62 |
| 5,110,743 A * | 5/1992 | Windisch et al. | 436/48 |
| 5,665,309 A * | 9/1997 | Champseix et al. | 422/63 |
| 5,918,979 A * | 7/1999 | Martin et al. | 366/211 |
| 6,627,156 B1 * | 9/2003 | Goodale et al. | 422/99 |
| 2001/0002985 A1 * | 6/2001 | Kleinsasser | 422/104 |
| 2001/0048894 A1 * | 12/2001 | Schmidt et al. | 422/63 |
| 2002/0021983 A1 * | 2/2002 | Comte et al. | 422/65 |
| 2005/0196320 A1 * | 9/2005 | Veiner et al. | 422/63 |
| 2006/0275177 A1 * | 12/2006 | Comte | 422/99 |
| 2007/0217951 A1 * | 9/2007 | Matsumoto | 422/67 |
| 2009/0158863 A1 * | 6/2009 | Shanafelter | 73/864.81 |

* cited by examiner

HEMATOLOGICAL ANALYZER ON WHOLE BLOOD WITH STIRRING DEVICE

FIELD OF THE INVENTION

The invention relates to the field of blood analysers intended for analysing samples of blood products automatically.

More particularly, it relates to a blood analyser for whole blood, for the analysis of bloods contained in tubes, wherein the tubes are brought and processed in a tube-by-tube mode.

BACKGROUND OF THE INVENTION

In the following, "operation in unitary mode" or "operation in tube-by-tube mode" are intended to mean a mode of operation in which the blood samples to be analysed are passed one after another, i.e. tube by tube, without the assembly of these tubes in cassette-type supports or the like.

By the expression "analysis of whole blood", it is intended to designate an analyser carrying out analyses on whole blood, i.e. containing all the elements of blood, as opposed to analysers operating on plasma or serum. Cell counters form part of whole blood analysers but the invention is not limited to only cell counters.

The expression "quality control" is used to mean a procedure which consists in checking at least daily that the analyser is working properly before carrying out analyses of blood samples from patients.

There are different types of blood analysers which carry out various types of analysis, including optical, physico-chemical analyses etc. on blood samples and which then automatically issue the results of analysis.

An essential condition for the correct functioning of these analysers is that the blood tubes have been previously correctly stirred during a stirring phase which precedes analysis.

In blood analysers operating in unitary mode or tube-by-tube mode, this stirring phase is often carried out manually, therefore in a more or less haphazard manner.

Consequently, when the user of the blood analyser is not familiar with laboratory practice, this preliminary phase of stirring may be carried out incorrectly, which may distort the results of the analysis.

This is often the case when the users are not specifically trained in laboratory practice.

SUMMARY OF THE INVENTION

The object of the invention is in particular to overcome these disadvantages by proposing to incorporate this stirring phase of the blood in a blood analyser for whole blood.

There are plural categories of analysers operating from whole blood. One of the biggest categories is that of cell counters, but the invention is not limited to this particular category.

Blood analysers are already known which operate not in tube-by-tube mode, but in a mode of assembly of tubes. In this case, the operator assembles the maximum number of tubes before starting analysis, which allows the operator to manage his time better and to securitise the tasks of identification and validation of the results.

In this case, the tubes are loaded into cassettes or trays before starting an automatic analysis cycle. It is therefore the blood analyser which undertakes stirring of the blood before analysis.

On the other hand, in blood analysers operating in unitary mode, the stirring phase is not carried out in the analyser itself. It is generally effected, either manually or in a separate stirrer or external stirrer operating for example by rotation or rocking. The operator has to wait a few minutes in order to obtain perfect stirring before starting the series of analyses. As the tubes are removed from the stirrer just before analysis, some tubes may remain there longer than others.

Furthermore, some laboratories use the time taken between two analyses to stir the next tube manually.

Some analysers operate in "open tube" mode, i.e. the operator takes the stirred tube and must remove the stopper before presenting the tube to the analyser.

Other analysers operate in "closed tube" mode, i.e. the stirred tube is presented directly to the analyser without prior opening. The analyser undertakes the piercing of the stopper in order to sample the blood inside the tube. This mode of operation makes it possible to protect the user against any risk of contact with the blood.

In all cases, prior stirring is necessary, even if the blood has only just been taken from the patient.

Analysers operating in unitary mode are mainly intended for small laboratories carrying out few analyses and are used jointly with an external stirrer.

Outside the sphere of the laboratory, there are many cases where it is necessary to carry out "analyses in the presence of the patient". This may respond to a need to obtain a rapid result, as in the case of emergency units.

This may also respond to a need for diagnosis, as is practised currently in certain countries, such as the United States or Japan, where doctors are enabled to carry out base analyses allowing them to consolidate their diagnosis.

This may also respond to the needs of remote medical centres where there are no laboratories nearby, as for example in medical facilities in rural areas, travelling medical units or military medical units.

In all these situations of "analyses in the presence of the patient", the operators tend to be doctors or nurses rather than qualified laboratory operators.

As these analyses are carried out on a very small amount of blood, it is necessary that this sampling is representative of the patient's blood and therefore that the content of the tube is perfectly homogeneous.

Outside the context of the laboratory, this prior stirring phase is sometimes omitted by lack of understanding of its importance, but usually because it is not an action which comes naturally in emergency conditions.

For reasons of practical organisation, it is not easy for an operator to place a tube of blood on a stirrer, then to come back and collect it to carry out the analysis, as a laboratory assistant would do after assembling the tubes to be analysed.

There is therefore a need to automate the stirring in a blood analyser for whole blood operating in unitary mode or tube-by-tube mode.

In the field of blood analysers operating by the assembly of tubes in cassette-type supports or the like, there are already means for carrying out automatic stirring.

Thus in the field of whole blood analysers with multiple supports in which tubes of blood are grouped, there are already stirring means. The U.S. Pat. No. 5,232,081 describes in particular a stirring device in which the mixing of blood samples is effected on a cassette-type support in which a large number of tubes [[a]] are assembled. However, this stirring device is only valid for apparatuses with multiple supports.

There are already known various stirring means, such as for example those indicated in the following non-limiting list:

stirring by complete inversion: this means consists in tipping up the tube of blood vertically plural times in succession. Mixing is effected during inversion when the blood passes from the bottom of the tube to the top of the tube, and vice versa when the tube is returned to its starting position. An example application is described in the U.S. Pat. No. 5,110,743;

stirring by partial inversion: in this case, the tube does not effect a complete revolution. The mixing principle is the same as that described above;

stirring by rocking motion: in this case, the tube is placed on a horizontal tray which effects a rocking motion. An example application is described in the U.S. Pat. No. 4,518,264;

stirring by rotation of the tube upon itself, known as the "vortex" effect: in this type of stirring, the tube remains in a vertical position. It is driven in rotation on its vertical axis in alternate directions.

The invention proposes a blood analyser of total blood operating in tube-by-tube manner, which aims to avoid the aforesaid disadvantages of analyses operating in tube-by-tube manner.

To this end, the analyser according to the invention comprises:

a stirring device contrived to receive one tube of blood and to stir this tube of blood according to a selected manner of stirring;

control means connected to the stirring device in order to stir the tube of blood in conditions controlled according to defined parameters; and means of sampling contrived to remove a sample of blood from the tube of blood previously stirred by the stirring device and to transfer the sample of blood towards an analysis block.

Thus the invention proposes a blood analyser incorporating a stirring device, which makes it possible to automate stirring, which is necessary before analysis, in order to guarantee the quality, including that for bloods intended for quality control.

Such a blood analyser is particularly advantageous in the case of routine laboratory apparatus, and in unitary apparatus used by operators carrying out "analyses in the presence of the patient".

However, the invention is also advantageous in apparatus used in laboratories, as it is thereby possible to combine types of stirring.

In all these cases, the blood analyser of the invention makes it possible to carry out stirring within the analyser itself, and not in a separate manner as in the prior art, and moreover in controlled conditions ensuring the quality of stirring.

In the invention, the tube of blood may be disposed manually in the stirring device. However, in a more developed version, the blood analyser may comprise displacement means adapted for transferring a tube of blood to the stirring device.

According to another feature of the invention, the stirring device comprises a receiving element for receiving a tube of blood either directly or via a support.

This receiving element may comprise either a single recess adapted to a tube of blood of specific shape, or plural recesses adapted respectively to different shapes of tubes of blood. However, in all cases, stirring is effected on a single tube of blood.

The control means of the analyser of the invention advantageously comprise means of programming in order to programme the duration of stirring of the stirring device. This makes it possible to effect stirring in well-controlled conditions.

The stirring device incorporated in the analyser of the invention is not limited to a particular embodiment.

However, in a preferred form of the invention, the stirring device comprises stirring means operating by a succession of complete inversions of the tube of blood, or stirring means operating by a succession of partial inversions of the tube of blood.

It is also possible to use stirring means operating by a succession of rocking motions of the tube of blood in a vertical plane.

In another modification, the stirring device comprises stirring means operating by a sequence comprising rotation of the tube of blood about a vertical axis with a specified direction of rotation, a halt in stirring, rotation of the tube of blood in the opposite direction about this vertical axis, and halting once more of stirring.

It is advantageous if the control means set a duration of stirring. This duration of stirring determines the number of full inversions of the tube of blood or the number of partial inversions of the tube of blood.

This duration of stirring also determines either the number of rocking motions of the tube of blood or the number of sequences of rotation and halting of rotation in the case of the above-mentioned modifications.

According to another feature of the invention, the stirring parameters of the control means may be set either directly on the blood analyser, or via an independent control station.

The stirring parameters are advantageously assembled in profiles of use.

According to another feature of the invention, the stirring device and the analysis block are contrived to operate simultaneously, which makes it possible to stir a tube of blood by stirring means while a previously stirred tube is being analysed by the analysis block.

The control means mentioned may also set a duration of stirring which is zero, so that it is possible not to carry out stirring.

In the invention, the tube of blood is conventionally sealed by a stopper.

It is advantageous in this case to provide an optical sensor placed inside the blood analyser in order to detect the presence or absence of a stopper on the tube of blood.

The sampling means advantageously comprise an element for piercing the stopper. This is preferably located directly above the tube to be pierced.

However, it is also conceivable to provide that the element for piercing the stopper is located below the tube to be pierced.

According to yet another feature of the invention, the blood analyser comprises internal or external connecting means for the exchange of securitised data.

BRIEF DESCRIPTION OF THE DRAWINGS

In the following description, given by way of example, the attached drawings are referred to, which show.

DESCRIPTION OF PREFERRED EMBODIMENTS

Figure 1:
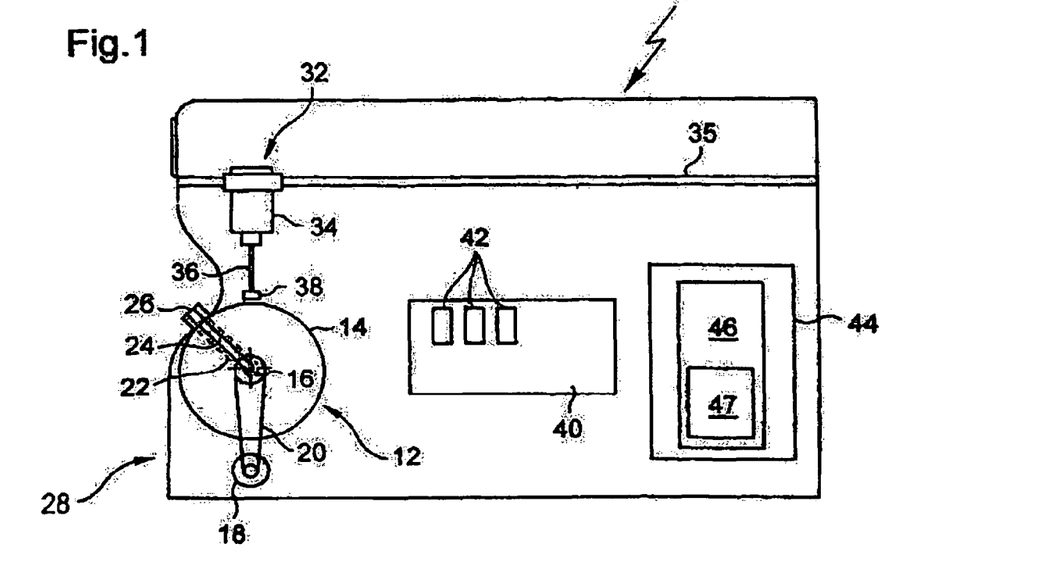
FIG. 1, a side view of a blood analyser with integral stirring device according to the invention.
Figure 2:
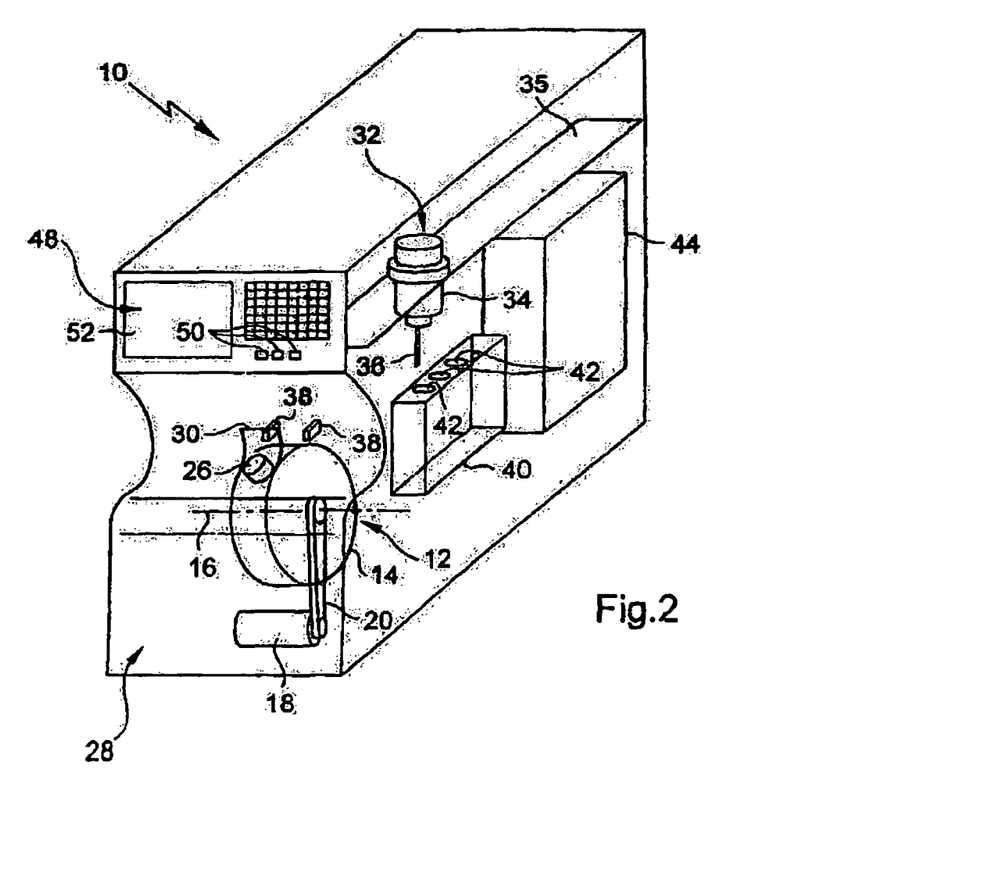
FIG. 2, a perspective view of the blood analyser of FIG. 1.

We refer first of all jointly to FIGS. 1 and 2, which show a blood analyser referenced 10 as a whole.

In the example, an analyser is used which is intended to count blood cells, which is one of the main applications of whole blood analysis. However, as is indicated above, the invention may be applied in all unitary analysers requiring whole blood previously stirred before analysis.

The analyser 10 incorporates a stirring device 12 which comprises a drum 14 mounted in rotation about a horizontal axis 16 and capable of being driven in rotation in either direction by an electric motor 18 of the stepper type having a transmission belt 20. The drum 14 comprises a recess 22 oriented radially (see also FIG. 4) which may receive a tube of blood 24 sealed by a stopper 26.

The stirring device 12 is located close to a front face 28 of the apparatus in which a window 30 is formed (FIG. 2) for the insertion of the tube 24 into the recess 22, the drum 14 being in a specified angular position. In the example, the recess forms an angle of about 45° relative to the horizontal, which permits the insertion of the tube into the recess. In the example, the tube is inserted manually, but may also be inserted automatically, as will be seen below.

The analyser 10 further comprises sampling means referenced 32 as a whole. These comprise a piercing block 34 displaceable along a horizontal rail 35. The piercing block comprises a sampling needle 36 disposed vertically, with its point oriented downwards. The piercing block is arranged to control displacement of the needle vertically, either in a downward direction in order to pierce the stopper 26 of a tube, or upwards once sampling has taken place. Sampling is effected in a position where the tube 24 is oriented vertically with its stopper oriented upwards.

The presence of the stopper 26 is detected by a sensor 38, which in the example is an optical sensor.

When the presence of a tube is detected, the piercing block 34 may come into action to pierce the stopper, and sample a specified quantity of blood from the tube. The piercing block 34 is displaceable along the rail in order to arrive then above an analysis block 40 comprising measuring receptacles 42, not described in detail, being means known per se.

The analyser 10 further comprises an automation unit 44 which comprises a control unit 46 for monitoring the operation of the analyser 10, as will be seen below. This control unit 46 may comprise in one embodiment a programming unit 47 for programming the operation of the analyser 10 and in particular for controlling the duration of stirring.

This automation unit is controlled from an interface 48 located in the upper part of the front face 28 and comprising buttons 50 and a monitoring screen 52.

Figure 3:
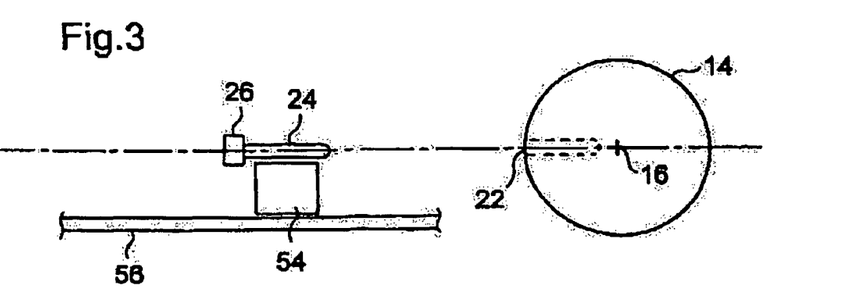
FIG. 3 shows a displacement device for inserting a tube of blood automatically into the stirring device.

We refer now to FIG. 3, which shows a modified embodiment of the invention in which the tube 24, closed by its stopper 26, is inserted into the recess 22 of the drum 14 by a displacement mechanism. These comprise a carriage 54 displaceable in both directions along a horizontal rail 56. In the example, the tube is displaced with its axis placed horizontally and is inserted into the recess 22, whose axis is also disposed horizontally.

Obviously, other types of displacement operating automatically are usable for inserting the tube automatically into the recess 22 of the drum 14.

In the invention, the tube of blood may be inserted directly into the reception housing (recess 22) of the drum 14 or indirectly via an individual support in which the tube of blood is placed at the start.

Figure 4:
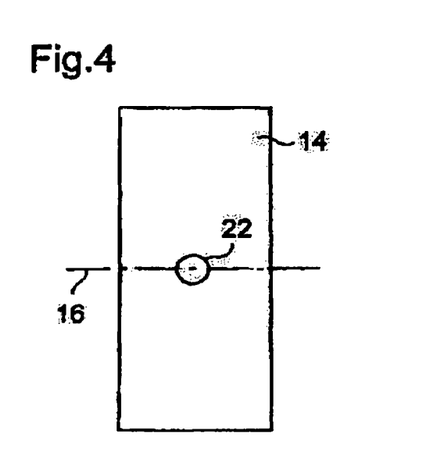
FIG. 4 shows a front view of a stirring drum comprising a single tube recess.

The drum 14 of FIG. 4 comprises a single recess 22 which is adapted for one tube of blood of a specified type (length and diameter).

However, there are different types of tube which differ in particular in dimensions (diameter and length).

Figure 5:
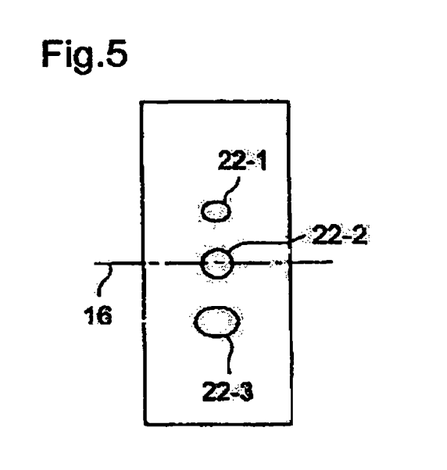
FIG. 5 is a view similar to FIG. 4 in a modified embodiment comprising plural recesses suitable for receiving tubes of different types.

The embodiment of FIG. 5 shows a drum 14 capable of receiving different types of tube. To this end, the drum comprises at its circumference plural recesses 22-1, 22-2 and 22-3 capable of being adapted respectively to three different types of tube. However, in all cases, stirring is carried out on one tube previously inserted into the matching recess.

Figure 6:
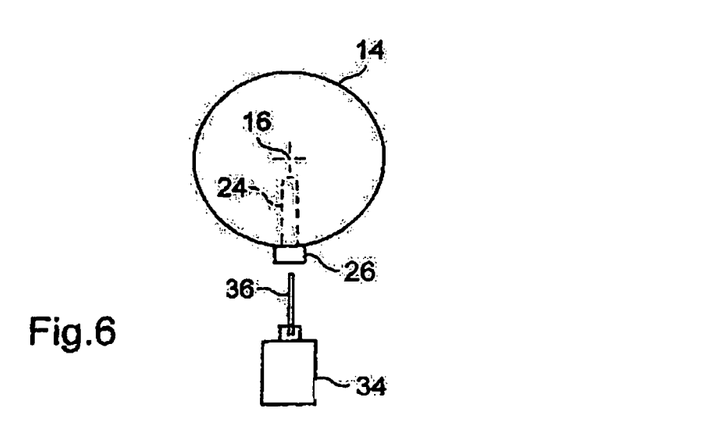
FIG. 6 is a side view of a stirring drum in which the tube piercing takes place from below.

FIG. 6, to which we now refer, shows another modified embodiment of the analyser 10 in which the piercing block 34 is placed below the drum 14, the sampling needle 36 being disposed vertically with its point oriented upwards. This makes it possible to pierce the stopper 26 of the tube 24 in a position where the stopper is oriented downwards.

However, it is also within the scope of the invention to effect piercing of the stopper in any specified angular position of the tube.

Figure 7:
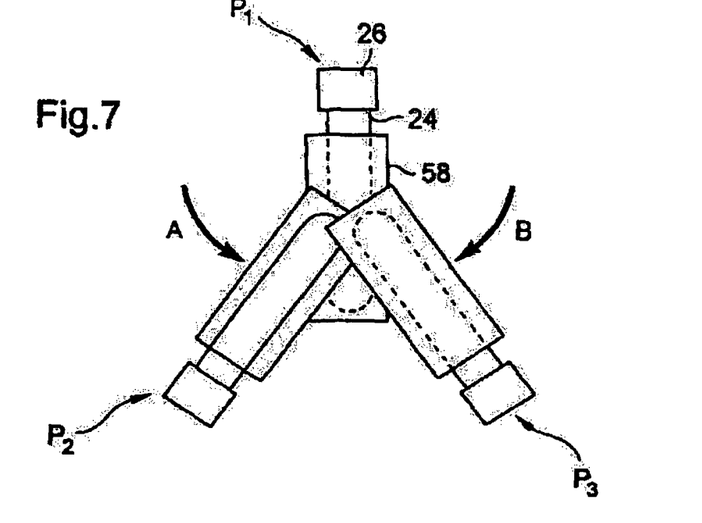
FIG. 7 shows the principle of a stirrer operating by partial inversion of the tubes.

In the embodiment shown in FIGS. 1 and 2, the stirring device 12 effects stirring by inversion, whose principle is illustrated in FIG. 7.

In the example, the tube 24 with its stopper 26 is inserted into an individual support 58 which may itself then be inserted into the drum 14 (not shown in FIG. 7). P1 represents the reference position (vertical position) with the stopper oriented upwards. In the example, stirring is effected by partial inversion which may be by a negative angle A as far as a position P2 or by a positive angle B as far as a position P3. The amplitude of the movement must be at least 100° up to an angle of 180° or at least −100° up to an angle of −180°. The number of inversions to be effected is generally between 10 and 20 to obtain correct stirring. Stirring may be effected by a succession of partial inversions (FIG. 7) or by a succession of full inversions, the amplitude of movement then being up to 180°.

However, the invention is not limited to stirring by inversion and other types of stirring are conceivable.

Figure 8:
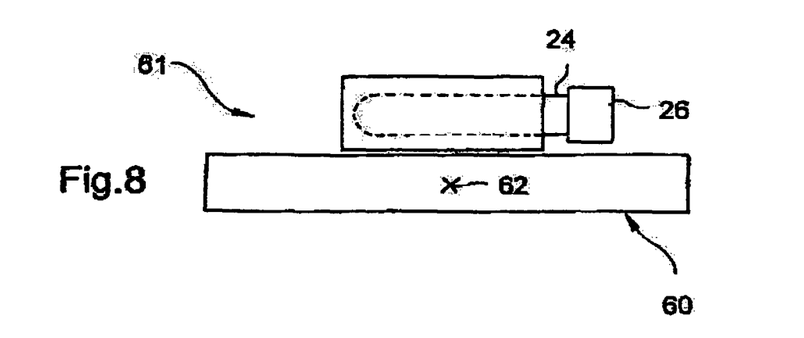
FIG. 8 shows a stirring device operating by rocking motion.

FIG. 8 shows diagrammatically a horizontal tray 60 mounted in rotation about a horizontal axis 62 and contrived to support a tube 24, the longitudinal axis of the tube being disposed horizontally and perpendicular to the axis 62. Such a tray makes it possible to effect a succession of rocking motions of the tube, these rocking motions being effected for example with an amplitude of 180° by alternate rotations between −90° and +90°.

Figure 9:
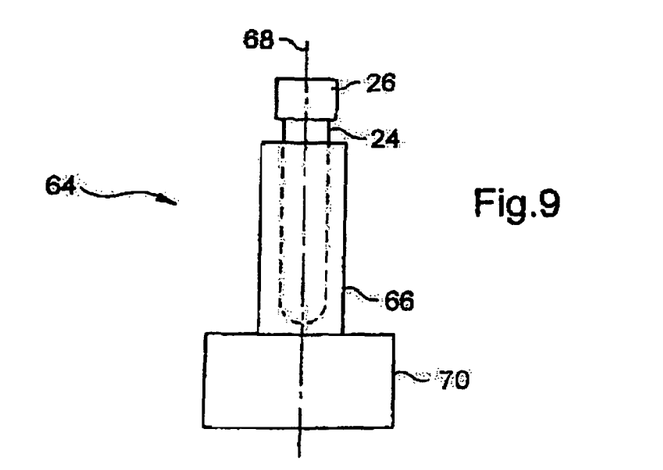
FIG. 9 shows a stirring device operating by rotation about a vertical axis.

FIG. 9 shows another stirring device 64 comprising a support 66 driven in rotation about a vertical axis 68 by a drive element 70, such as an electric stepper-type motor. The support 66 is contrived to receive a tube 24 in a vertical position, with the stopper 26 oriented upwards, the longitudinal axis of the tube coinciding with the vertical axis 68 of rotation. The device 64 is contrived to effect a sequence comprising rotation of the tube of blood about the vertical axis 68 in a specified direction of rotation, halting of stirring, rotation of the tube of blood about the vertical axis in the opposite direction, and halting again of stirring and so on.

In all these cases, the control means (control unit 46) set a stirring duration which determines either the number of full or partial inversions of the tube of blood (stirring device 12), or the number of rocking motions of the tube of blood (stirring device 61), or the number of sequences of rotations and halts in rotation (stirring device 64).

The modus operandi of the analyser 10 is described below.

First of all, the tube of blood 24 is placed in the stirring device either manually or automatically as is indicated above.

The sensor 38 detects the presence or absence of the stopper 26. The operation of the stirring device is conditioned by the detection of a stopper 26 by the sensor 38.

Then the stirring of the tube of blood is effected in controlled conditions, and with defined parameters, under the control of the control unit 46.

Once stirring has been effected, the tube of blood is once more in the position of FIGS. 1 and 2, with its stopper oriented upwards.

The piercing block 34 is then placed automatically above the stopper 26 and the needle 36 is moved vertically downwards to pierce the stopper and permit the taking of a sample of blood. Sampling is effected according to the type of analysis to be carried out. It is often accompanied by a means of ventilating the tube of blood before sampling so as to remove a precise quantity of blood.

The piercing block 34 is then displaced to be brought above the analysis block and then to release a specified quantity of the sample through the needle 36 into a measuring receptacle 42. The analyses are then effected by the analysis block 40 in a conventional manner, and the results are supplied to the unit 44. To this end, the analyser according to the invention comprises internal or external connecting means (not shown) for the exchange of securitised data.

The tube 24 is advantageously returned to the user when the operations of stirring and sampling are finished, and without waiting for the analysis being carried out to be completed.

It is advantageous that the stirring device and the analysis block are contrived to operate simultaneously, so as to stir a tube of blood while a previously stirred tube is being analysed.

Thus another tube can be put in place to be stirred while the previous analysis is being carried out, which makes it possible not to waste any time when the operator has to put a plurality of tubes through in succession.

The analyser according to the invention also makes it possible to adjust the duration of stirring according to the tube to be analysed, this duration determining the number of stirring motions, as is indicated above.

The criteria for selecting the duration of stirring depend on the type of stirring taken into account. A factor representing the shape of the tube can be taken into account, being more or less favourable to a specified type of stirring. One may also take into account a factor relating to the type of blood to be analysed, whether it be a human blood, an animal blood, or a control or calibration blood. One can take into account a factor relating to the blood itself at the moment of analysis. One can select, for example, a longer duration for a blood which has been kept for a long period in the refrigerator or a shorter duration for a blood which has been taken just before testing.

In the analyser of the invention, the stirring device can be associated with means of preserving samples intended for quality control and for calibration of the analyser.

The invention also makes it possible to control the speed of the stirring means, e.g. the speed of inversion in the case of stirring by full or partial inversion, or the speed of rocking motion in the case of stirring by rocking motion.

The parameters of stirring, such as its duration or speed, can be defined either directly on the blood analyser by means of buttons 50 and the monitoring screen 52, or via a control station connected to the analyser.

The values associated with the parameters of a specified stirring can be grouped and recorded in the form of profiles as a simple way of making the analysis conditions uniform.

For example, one profile can be drawn for bloods taken from the refrigerator or another for bloods taken just before from the patient.

The duration of stirring can also be set to a zero value, which makes it possible to cancel the stirring sequence.

It is also possible to provide that the analyser does not start the analysis before the period of stirring has completely finished. This becomes important when the analyses follow one after another, without waiting for the end of the cycle, to the extent that the operator can insert the next tube at any moment.

Figure 10:
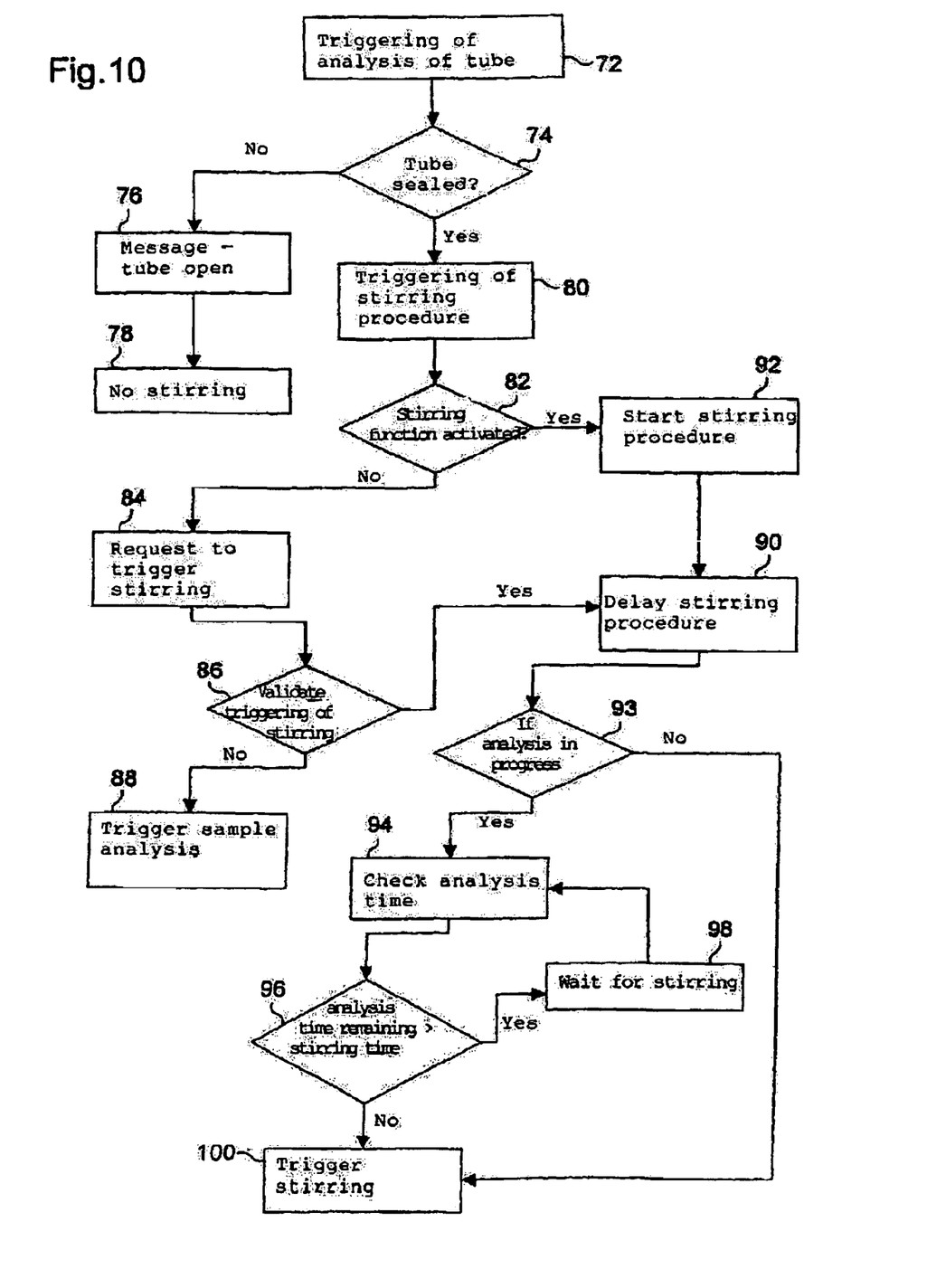
FIG. 10 is a diagram showing, in the form of a flow-chart, the operation of a blood analyser according to the invention.

The algorithm shown in FIG. 10 describes the monitoring of the stirring device integral with the analyser.

The procedure starts at stage 72 with the start of analysis of the tube. At the next stage 74, a comparison is carried out to determine whether the tube is sealed or not. This information comes from the sensor 38. If the tube is not sealed, a message "tube open" is displayed at stage 76 and no stirring is carried out, as is mentioned at stage 78.

If the tube is sealed, the stage 80 triggers the stirring procedure.

At the next stage 82, a comparison is carried out to determine whether the stir function is activated.

If negative, a request to start stirring is made at stage 84. Then, at stage 86, a comparison is carried out to validate the start of stirring.

If negative, the start of analysis of the sample is triggered at stage 88. If affirmative, a stage 90 of stirring and procedure for time delay is triggered.

Furthermore, if the comparison of the stir function activated in stage 82 is positive, the start of the stirring procedure is effected at stage 92, and this ends with the stage 90 mentioned above.

Following stage 90, at stage 93, a comparison is made to find out whether an analysis is under way.

If affirmative, the stage 94 checks the time of analysis.

At the next stage 96, a comparison is made to determine whether the remaining analysis time is longer than the stirring time.

If affirmative, a stage 98 of waiting for stirring is carried out and this stage returns to stage 94.

If negative, stirring is triggered at stage 100.

Stirring can also be triggered starting from stage 93 if the response is negative.

Obviously, the invention is not limited to the embodiments described above by way of example, and other modified embodiments are conceivable, in particular relating to the kind of stirring means used.

The invention claimed is:

1. An integrated blood analyzer of whole blood contained in tubes, comprising:
    a single tube of blood;
    a drum that is configured to receive and hold the single tube of blood and to stir the single tube of blood by inversion, wherein the single tube of blood is stirred individually without assembly of the single tube of blood in a cassette support, the drum includes a plurality of recesses extending into the drum, each recess is of a different diameter to fit various sized tubes of blood, the stirring being carried out individually for the single tube of blood inserted into the respective recess;

a controller connected to the drum to stir the single tube of blood by inversion in conditions controlled according to defined variable parameters, the defined variable parameters including variable values of at least one of stirring duration, a number of inversions, and a speed of inversion;

an analysis unit performing analysis of the sample of blood from the singe tube of blood;

an optical sensor located adjacent to the drum and configured to detect the presence of a stopper on the single tube of blood;

a sampling means including;
- a needle configured to aspirate the blood sample from the single tube in the drum and pierce the stopper when the stopper is detected by the optical sensor, and
- a horizontal rail along which the sampling means moves to aspirate the sample of blood from the single tube of blood held in the drum and previously stirred by the drum and to move along the rail away from the drum to dispense the sample of blood into the analysis unit performing analysis of the sample of blood.

2. The blood analyzer according to claim 1, wherein the defined variable parameters of the controller may be set either directly on the blood analyzer, or through an independent control station.

3. The blood analyzer according to claim 2, wherein the defined parameters are assembled into profiles of use.

4. The blood analyzer according to claim 1, wherein the drum and the analysis unit are configured to operate simultaneously, which makes it possible to stir the single tube of blood by the drum while a previously stirred single tube is being analyzed by the analysis unit.

5. The blood analyzer according to claim 1, wherein the needle is located directly above the tube to be pierced.

6. The blood analyzer according to claim 1, wherein the needle is located directly below the tube to be pierced.

7. The blood analyzer according to claim 1, further comprising a displacement mechanism to insert the single tube of blood into the drum.

8. The blood analyzer according to claim 1, further comprising a housing with an input window adjacent to the drum, for insertion of the single tube of blood through the input window into the drum.

* * * * *